(12) United States Patent
Reiley et al.

(10) Patent No.: US 7,044,954 B2
(45) Date of Patent: May 16, 2006

(54) METHOD FOR TREATING A VERTEBRAL BODY

(75) Inventors: Mark A Reiley, Piedmont, CA (US); Arie Scholten, Fremont, CA (US); Karen D Talmadge, Palo Alto, CA (US); Robert M Scribner, Los Altos, CA (US); Michael L Reo, Redwood City, CA (US)

(73) Assignee: Kyphon Inc., Sunnyvale, CA (US)

( * ) Notice: Subject to any disclaimer, the term of this patent is extended or adjusted under 35 U.S.C. 154(b) by 447 days.

(21) Appl. No.: 09/884,365

(22) Filed: Jun. 19, 2001

(65) Prior Publication Data

US 2001/0041896 A1    Nov. 15, 2001

Related U.S. Application Data

(63) Continuation of application No. 08/911,805, filed on Aug. 15, 1997, now abandoned, which is a continuation-in-part of application No. 08/871,114, filed on Jun. 9, 1997, now Pat. No. 6,248,110, which is a continuation-in-part of application No. 08/659,678, filed on Jun. 5, 1996, now Pat. No. 5,827,289, which is a continuation-in-part of application No. 08/485,394, filed on Jun. 7, 1995, now abandoned, which is a continuation-in-part of application No. 08/188,224, filed on Jan. 26, 1994, now abandoned.

(51) Int. Cl.
*A61B 17/58* (2006.01)

(52) U.S. Cl. .......................................... 606/93; 606/192
(58) Field of Classification Search ................ 606/192, 606/94; 600/207; 604/96.01
See application file for complete search history.

(56) References Cited

U.S. PATENT DOCUMENTS

| | | | |
|---|---|---|---|
| 3,626,949 A | | 12/1971 | Shute |
| 3,997,138 A | | 12/1976 | Crock et al. |
| 4,367,816 A | | 1/1983 | Wilkes |
| 4,369,772 A | | 1/1983 | Miller |
| 4,432,358 A | | 2/1984 | Fixel |
| 4,490,421 A | * | 12/1984 | Levy ....................... 604/96.01 |
| 4,653,489 A | | 3/1987 | Tronzo |
| 4,772,287 A | | 9/1988 | Ray et al. |

(Continued)

OTHER PUBLICATIONS

Kunec, J.R., et al., Closed Intramedullary Rodding of Pathologic Fractures with Supplemental Cement, Clinical Ortho-paedics and Related Research, vol. 188 pp. 183-186 (Sep. 1984).

(Continued)

*Primary Examiner*—Julian W. Woo
(74) *Attorney, Agent, or Firm*—Ryan Kromholz & Manion, S.C.

(57) ABSTRACT

A structure adapted to assume an expanded geometry having a desired configuration when used in bone includes material that limits the expanded geometry. The structure undergoes stress when expanded during its first use in bone. As a result, the structure can not be relied upon to reach its desired configuration during subsequent use in bone. Accordingly, the structure is packaged in a sterile kit, which verifies to the physician or user that the device packaged within it is sterile and has not be subjected to prior use. The physician or user is thereby assured that the expandable structure meets established performance and sterility specifications, and will have the desired configuration when expanded for use.

7 Claims, 9 Drawing Sheets

U.S. PATENT DOCUMENTS

| | | | |
|---|---|---|---|
| 4,969,888 | A | 11/1990 | Scholten et al. |
| 4,987,892 | A | 1/1991 | Krag et al. |
| 5,015,255 | A | 5/1991 | Kuslich |
| 5,062,845 | A | 11/1991 | Kuslich et al. |
| 5,108,404 | A * | 4/1992 | Scholten et al. ............ 606/94 |
| 5,127,912 | A | 7/1992 | Ray et al. |
| 5,176,692 | A | 1/1993 | Wilk et al. |
| 5,331,975 | A | 7/1994 | Bonutti |
| 5,403,340 | A * | 4/1995 | Wang et al. ............ 604/96.01 |
| 5,445,639 | A | 8/1995 | Kuslich et al. |
| 5,549,388 | A | 8/1996 | Wilkes |
| 5,549,679 | A | 8/1996 | Kuslich |
| 5,788,703 | A | 8/1998 | Mittelmeier et al. |
| 6,235,043 | B1 | 5/2001 | Reiley et al. |
| 6,248,110 | B1 | 6/2001 | Reiley et al. |

OTHER PUBLICATIONS

Campbells' Operative Orthopaedics, A.H. Crenshaw, Ed., 7$^{th}$ ed., Chapter 44, pp. 1653-1663 (1987).

Carlson, "The Use of Methylmahacrylate in Repair of Neoplastic Lesions in Bone," Radiology, vol. 112, pp. 43-46 (Jul. 1974).

Daniaux, H., "Technik und Ergebnisse der Transpedikularen Spongiosaplastick Bei Kompressionsbruchen im Lendenwirbalsaulenbereich" Acta Chir. Austr. (Suppl.), vol. 43, pp. 79-80 (1982) (with English Translation).

Daniaux, H., "Transpedikulare Reposition unde erste Spongiosaplastik Bei Wirbelkorparbruchen der Unteren Brust und Lendenwirbelsaule," Unfallchirung, vol. 89, pp. 197-213 (1986) (with English Translation).

Dick, W., "Use of the Actebular Reamer to Harvest Autogenic Bone Graft Material: A Simple Method for Producing Bone Paste," Arch. Orthop. Trauma Surg., vol. 105, pp. 234-238 (1986).

Dick, W., "The Fixaturer Interne' as Versatile Implant for Spine Surgery," Spine, vol. 12(9), pp. 882-900 (1987).

Edeland, H.G., "Open Reduction of Central Compression Fractures of the Tibia Plateau," Acta Orthop. Scand., vol. 47, pp. 686-689 (1976).

Kennedy, W., "Fracture of the Tibia Condyles: A Preliminary Report of Supplementary Fixation with Methylmethacrylate," Clin. Orthop., vol. 143, pp. 153-157 (1978).

Ma, Yuan-zhang, 'Os Calsis Fracture Treated by Percutaneous Poking Reduction and Internal Fixation,' Chinese Medical J., vol. 97, No. 2, pp. 105-110 (1984).

Olerud, S., "Transpedicular Fixation of Toracolumar Vertebral Fractures," Clin. Orthop., vol. 227, pp. 44-51 (1988).

Pantelenyi, T., "First Hungarian Neurosurgical Experiences with 'Fixateur Interne' in the Treatment of Thoraco-Lumbar Spine Injuries," Acta Neurochir. (Wian), vol. 93, pp. 104-109 (1988).

Schatzker, J., Operative Orthopaedics, M. Chapman, Ed., 1$^{st}$ ed., Ch. 35, pp. 421-434 (1998).

Scoville, W., "The Use of Acrylic Plastic for Vertebral Replacement of Fixation in Mestastic Disease of the Spine," J. Neurosurg., vol. 27: 274-79 (Sep. 1967).

* cited by examiner

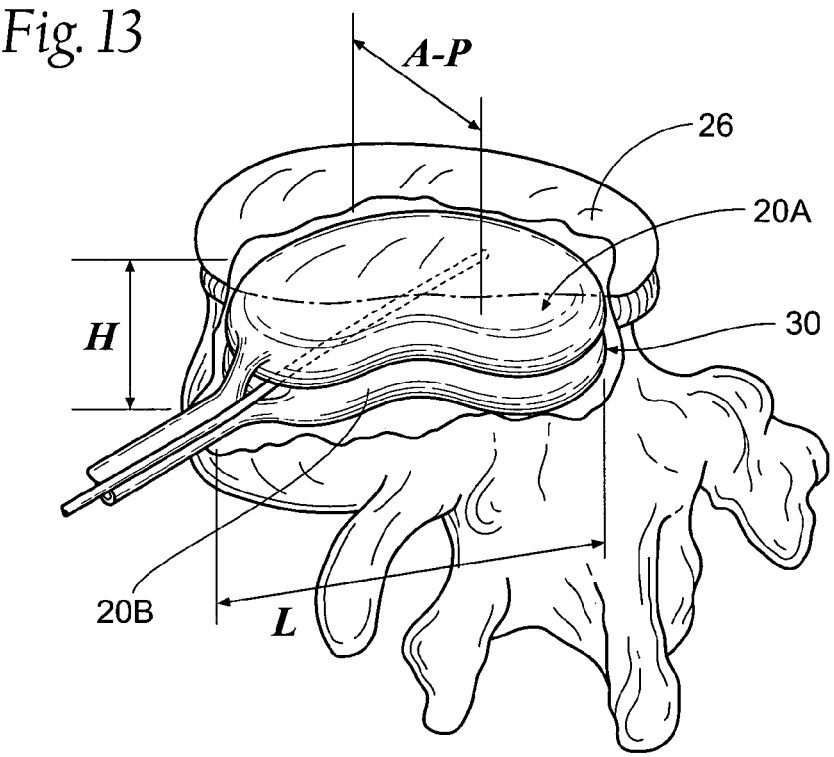

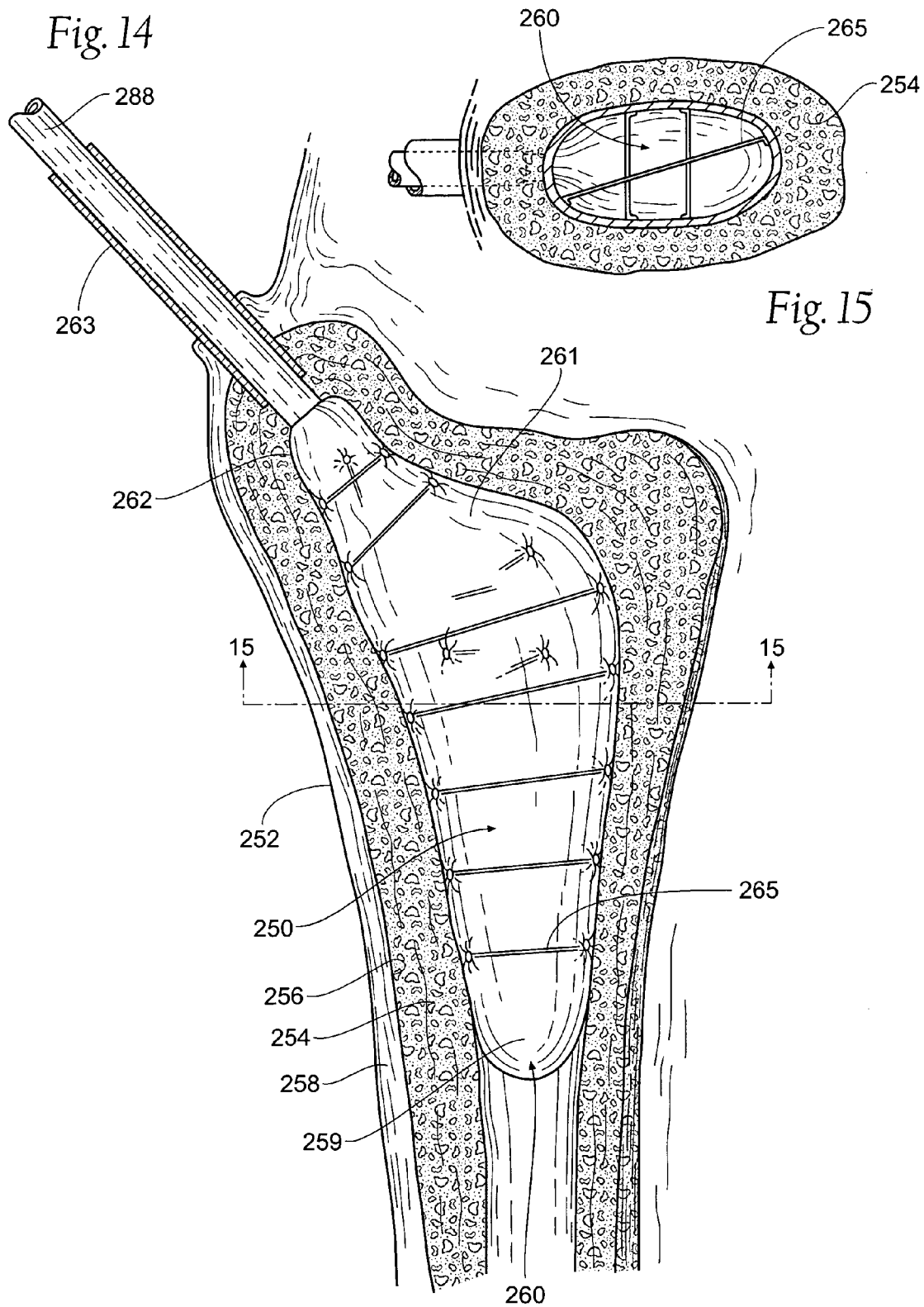

METHOD FOR TREATING A VERTEBRAL BODY

RELATED APPLICATIONS

This application is a continuation of application Ser. No. 08/911,805 filed Aug. 15, 1997, now abandoned which is a continuation-in-part of U.S. patent application Ser. No. 08/871,114, filed Jun. 9, 1997, now U.S. Pat. No. 6,248,110 which is a continuation-in-part of U.S. patent application Ser. No. 08/659,678, filed Jun. 5, 1996, now U.S. Pat. No. 5,827,289, which is a continuation-in-part of U.S. patent application Ser. No. 08/485,394, filed Jun. 7, 1995, now abandoned which is a continuation-in-part of U.S. patent application Ser. No. 08/188,224, filed Jan. 26, 1994, now abandoned entitled, "Improved Inflatable Device For Use In Surgical Protocol Relating To Fixation Of Bone".

FIELD OF THE INVENTION

The invention relates to the treatment of bone conditions in humans and other animals.

BACKGROUND OF THE INVENTION

When cancellous bone becomes diseased, for example, because of osteoporosis, avascular necrosis, or cancer, the surrounding cortical bone becomes more prone to compression fracture or collapse. This is because the cancellous bone no longer provides interior support for the surrounding cortical bone.

There are 2 million fractures each year in the United States, of which about 1.3 million are caused by osteoporosis alone. There are also other bone disease involving infected bone, poorly healing bone, or bone fractured by severe trauma. These conditions, if not successfully treated, can result in deformities, chronic complications, and an overall adverse impact upon the quality of life.

U.S. Pat. Nos. 4,969,888 and 5,108,404 disclose apparatus and methods for the fixation of fractures or other conditions of human and other animal bone systems, both osteoporotic and non-osteoporotic. The apparatus and methods employ an expandable body to compress cancellous bone and provide an interior cavity. The cavity receives a filling material, which hardens and provides renewed interior structural support for cortical bone.

The better and more efficacious treatment of bone disease that these Patents promise can be more fully realized with improved systems and methods for making and deploying expandable bodies in bone.

SUMMARY OF THE INVENTION

A method selects a vertebral body for treatment having a cortical wall enclosing a cancellous bone volume. The method provides a void creation device including an expandable structure adapted to undergo expansion in the cancellous bone volume. The expandable structure has at least one dimension so that the expandable structure will assume a predetermined shape and size when substantially expanded that compacts only a first volume of the cancellous bone volume to form a void, leaving a second volume of the cancellous bone volume substantially uncompacted by the expandable structure. The method introduces the void creation device into the vertebral body through a percutaneous access path. The method expands the expandable structure in the cancellous bone volume to the predetermined shape and size to create the void. The method leaves the second volume of the cancellous bone volume substantially uncompacted by the expandable structure. The method places a filling material within the void through the percutaneous access path.

Features and advantages of the inventions are set forth in the following Description and Drawings, as well as in the appended Claims.

BRIEF DESCRIPTION OF THE DRAWINGS

FIG. 13 is a perspective, lateral view of a vertebral body, partially broken away to show the presence of an expandable structure, and also showing the major reference dimensions for the expandable structure;

FIG. 14 is a dorsal view of a representative expandable structure having a humpback banana-shaped geometry in use in a right distal radius;

FIGS. 15 is a cross sectional view of the expandable structure shown in FIG. 14, taken generally along line 15—15 of FIG. 14;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The preferred embodiment describes improved systems and methods that embody features of the invention in the context of treating bones. This is because the new systems and methods are advantageous when used for this purpose. It should be appreciated that the systems and methods as described are not limited to use in the treatment of bones.

I. The Expandable Structure

Figure 1:
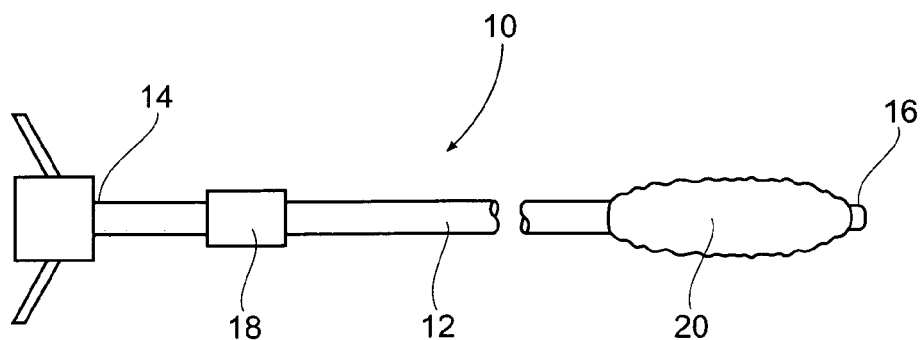
FIG. 1 is a plan view of a probe that carries an expandable structure that embodies features of the invention.

FIG. 1 shows a tool 10, which includes a catheter tube 12 having a proximal and a distal end, respectively 14 and 16. The catheter tube 12 includes a handle 18 near its proximal end 14 to facilitate gripping and maneuvering the tube 12. The handle 18 is preferably made of a foam material secured about the catheter tube 12.

The distal end 16 carries an expandable structure 20. The structure 20 is shown in FIG. 1 in a substantially collapsed geometry. When substantially collapsed, the structure 20 can be inserted into the interior of a bone, as will be described in greater detail later.

Generally speaking (and as will be demonstrated in greater detail later), an animal bone includes an exterior formed from compact cortical bone, which encloses an interior volume of reticulated cancellous, or spongy, bone (also called medullary bone or trabecular bone). When collapsed, the structure 20 is deployed in the cancellous bone.

As will also be described in greater detail later, the structure 20, when expanded, compresses the cancellous bone and thereby creates an interior cavity. The cavity is intended to receive a filling material, e.g., bone cement, which hardens and provides renewed interior structural support for surrounding cortical bone. The compaction of cancellous bone also exerts interior force upon cortical bone, making it possible to elevate or push broken and compressed bone back to or near its original prefracture, or other desired, condition.

U.S. Pat. Nos. 4,969,888 and 5,108,404 disclose the use of expandable structures for the fixation of fractures or other conditions of human and other animal bone systems, both osteoporotic and non-osteoporotic. These Patents are incorporated herein by reference.

A. Material Selection for the Expandable Structure

The material of the expandable structure 20 can be selected according to the therapeutic objectives surrounding its use. For example, materials including vinyl, nylon, polyethylenes, ionomer, polyurethane, and polyethylene tetraphthalate (PET) can be used. The thickness of the structure is typically in the range of $2/1000$ths to $25/1000$ths of an inch, or other thicknesses that can withstand pressures of up to, for example, 250–500 psi.

If desired, the material for the structure 20 can be selected to exhibit generally elastic properties, like latex. Alternatively, the material can be selected to exhibit less elastic properties, like silicone. Using expandable bodies with generally elastic or generally semi-elastic properties, the physician monitors the expansion to assure that over-expansion and wall failure do not occur. Furthermore, expandable bodies with generally elastic or generally semi-elastic properties may require some form of external or internal restraints to assure proper deployment in bone. The use of internal or external restraints in association with expandable bodies used to treat bone is discussed in greater detail in copending U.S. patent application Ser. No. 08/485,394, filed Jun. 7, 1995, which is incorporated herein by reference.

Generally speaking, for use in treating bone, providing relatively inelastic properties for the expandable structure 20, while not always required, is nevertheless preferred, when maintaining a desired shape and size within the bone is important, for example, in a vertebral structure, where the spinal cord is nearby. Using relatively inelastic bodies, the shape and size can be better predefined, taking into account the normal dimensions of the outside edge of the cancellous bone. Use of relatively inelastic materials also more readily permits the application of pressures equally in a defined geometry to compress cancellous bone.

When treating bone, the choice of the shape and size of a expandable structure 20 takes into account the morphology and geometry of the site to be treated. The shape of the cancellous bone to be compressed, and the local structures that could be harmed if bone were moved inappropriately, are generally understood by medical professionals using textbooks of human skeletal anatomy along with their knowledge of the site and its disease or injury. The physician is also able to select the materials and geometry desired for the structure 20 based upon prior analysis of the morphology of the targeted bone using, for example, plain films, spinous process percussion, or MRI or CRT scanning. The materials and geometry of the structure 20 are selected to optimize the formation of a cavity that, when filled with bone cement, provide support across the middle region of the bone being treated.

In some instances, it is desirable, when creating a cavity, to also move or displace the cortical bone to achieve the desired therapeutic result. Such movement is not per se harmful, as that term is used in this Specification, because it is indicated to achieve the desired therapeutic result. By definition, harm results when expansion of the structure 20 results in a worsening of the overall condition of the bone and surrounding anatomic structures, for example, by injury to surrounding tissue or causing a permanent adverse change in bone biomechanics.

As one general guideline, the selection of the geometry of the expandable structure 20 should take into account that at least 40% of the cancellous bone volume needs to be compacted in cases where the bone disease causing fracture (or the risk of fracture) is the loss of cancellous bone mass (as in osteoporosis). The preferred range is about 30% to 90% of the cancellous bone volume. Compacting less of the cancellous bone volume can leave too much of the diseased cancellous bone at the treated site. The diseased cancellous bone remains weak and can later collapse, causing fracture, despite treatment.

Another general guideline for the selection of the geometry of the expandable structure 20 is the amount that the targeted fractured bone region has been displaced or depressed. The expansion of the structure 20 within the cancellous bone region inside a bone can elevate or push the fractured cortical wall back to or near its anatomic position occupied before fracture occurred.

However, there are times when a lesser amount of cancellous bone compaction is indicated. For example, when the bone disease being treated is localized, such as in avascular necrosis, or where local loss of blood supply is killing bone in a limited area, the expandable structure 20, can compact a smaller volume of total bone. This is because the diseased area requiring treatment is smaller.

Another exception lies in the use of an expandable structure 20 to improve insertion of solid materials in defined shapes, like hydroxyapatite and components in total joint replacement. In these cases, the structure 20 shape and size is defined by the shape and size of the material being inserted.

Yet another exception lays the use of expandable bodies in bones to create cavities to aid in the delivery of therapeutic substances, as disclosed in copending U.S. patent application Ser. No. 08/485,394, previously mentioned. In this case, the cancellous bone may or may not be diseased or adversely affected. Healthy cancellous bone can be sacrificed by significant compaction to improve the delivery of a drug or growth factor which has an important therapeutic purpose. In this application, the size of the expandable structure 20 is chosen by the desired amount of therapeutic substance sought to be delivered. In this case, the bone with the drug inside is supported while the drug works, and the bone heals through exterior casting or current interior or exterior fixation devices.

The materials for the catheter tube are selected to facilitate advancement of the expandable structure 20 into cancellous bone. The catheter tube can be constructed, for example, using standard flexible, medical grade plastic materials, like vinyl, nylon, polyethylenes, ionomer, polyurethane, and polyethylene tetraphthalate (PET). The catheter tube can also include more rigid materials to impart greater stiffness and thereby aid in its manipulation. More rigid materials that can be used for this purpose include stainless steel, nickel-titanium alloys (Nitinol™ material), and other metal alloys.

B. Selection of Shape and Size for the Expandable Structure

As will also be demonstrated later, when relatively inelastic materials are used for the structure 20, or when the structure 20 is otherwise externally restrained to limit its expansion prior to failure, a predetermined shape and size can be imparted to the structure 20, when it is substantially expanded. The shape and size can be predetermined according to the shape and size of the surrounding cortical bone 28 and adjacent internal structures, or by the size and shape of the cavity desired to be formed in the cancellous bone 32.

In one embodiment, which is generally applicable for treating bones experiencing or prone to fracture, the shape and size of the structure 20, when substantially expanded, can be designed to occupy at least about 30% of the volume of cancellous bone 32 in the interior volume 30. A structure 20 having a substantially expanded size and shape in the range of about 40% to about 99% of the cancellous bone volume is preferred.

In another embodiment, which is applicable for treating bones having more localized regions of fracture or collapse caused, for example, by avascular necrosis, the shape and size of the structure 20 can be designed to occupy as little as about 10% of the cancellous bone volume. In this embodiment, the structure 20 is deployed directly at the localized site of injury.

The shape of the cancellous bone 32 to be compressed, and the presence of surrounding local anatomic structures that could be harmed if cortical bone were moved inappropriately, are generally understood by medical professionals using textbooks of human skeletal anatomy, along with their knowledge of the site and its disease or injury. The physician is also able to select the materials and geometry desired for the structure 20 based upon prior analysis of the morphology of the targeted bone using, for example, plain films, spinous process percussion, or MRI or CRT scanning. The materials and geometry of the structure 20 are selected to create a cavity of desired size and shape in cancellous bone without applying harmful pressure to the outer cortical bone or surrounding anatomic structures.

In some instances, it is desirable, when creating the cavity, to move or displace the cortical bone to achieve the desired therapeutic result. Such movement is not per se harmful, as that term is used in this Specification, because it is indicated to achieve the desired therapeutic result. By definition, harm results when expansion of the structure 20 results in a worsening of the overall condition of the bone and surrounding anatomic structures, for example, by injury to surrounding tissue or causing a permanent adverse change in bone biomechanics.

II. Treatment of Vertebral Bodies

Figure 2:
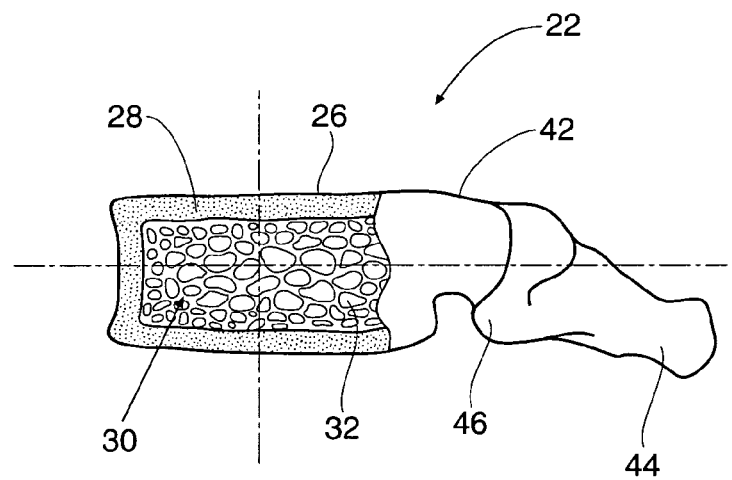
FIG. 2 is a lateral view, partially broken away and in section, of a lumbar vertebra.
Figure 3:
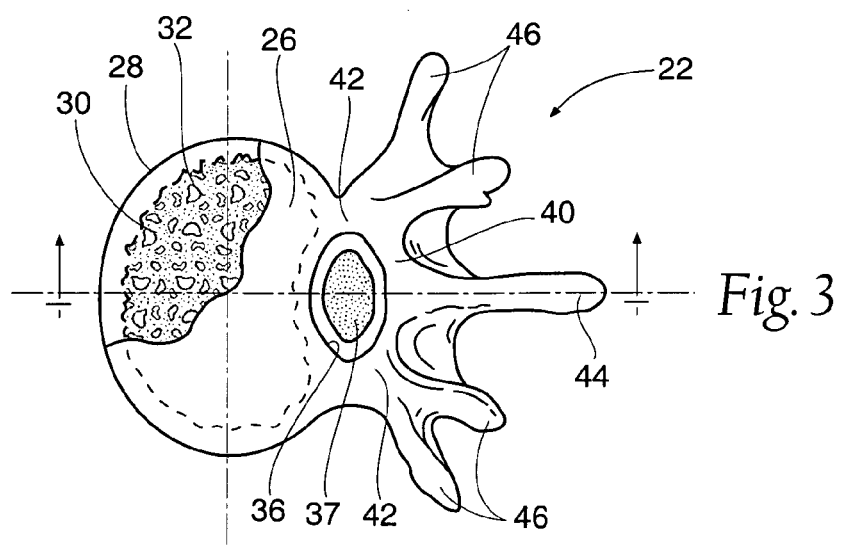
FIG. 3 is a coronal view of the lumbar vertebra, partially cut away and in section, shown in FIG. 2.

FIG. 2 shows a lateral (side) view of a human lumbar vertebra 22. FIG. 3 shows a coronal (top) view of the vertebra 22. The vertebra 22 includes a vertebral body 26, which extends on the anterior (i.e., front or chest) side of the vertebra 22. The vertebral body 26 is in the shape of an oval disk.

As FIGS. 2 and 3 show, the vertebral body 26 includes an exterior formed from compact cortical bone 28. The cortical bone 28 encloses an interior volume 30 of reticulated cancellous, or spongy, bone 32 (also called medullary bone or trabecular bone).

The spinal canal 36 (see FIG. 2), is located on the posterior (i.e., back) side of each vertebra 22. The spinal cord 37 passes through the spinal canal 36. The vertebral arch 40 surrounds the spinal canal 36. Left and right pedicles 42 of the vertebral arch 40 adjoin the vertebral body 26. The spinous process 44 extends from the posterior of the vertebral arch 40, as do the left and right transverse processes 46.

Figure 4:
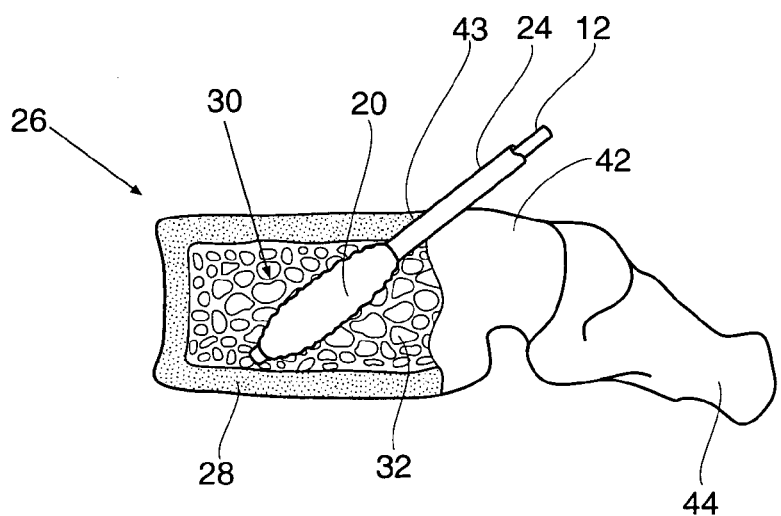
FIG. 4 is a lateral view of the lumbar vertebra shown in FIGS. 2 and 3, partially cut away and in section, with the expandable structure shown in FIG. 1 deployed by transpedicular access when in a substantially collapsed condition.
Figure 5:
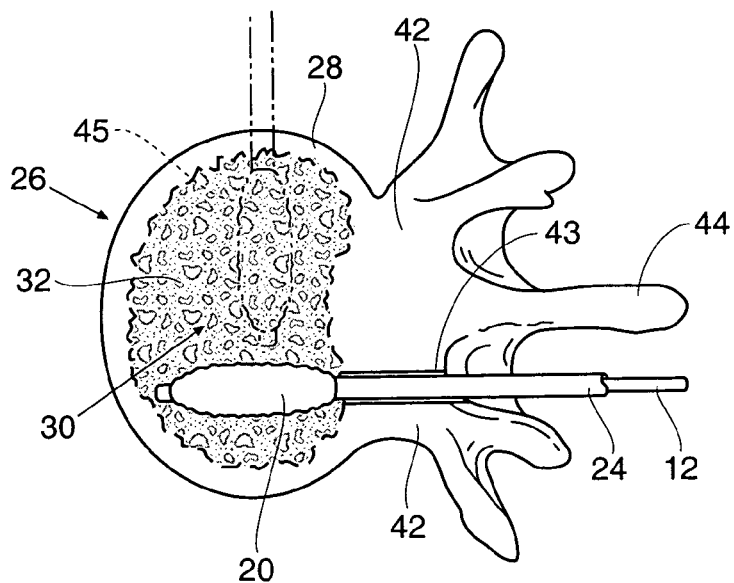
FIG. 5 is a coronal view of the transpedicular access shown in FIG. 4, partially cut away and in section.

A selected expandable structure 20 can be inserted into bone in accordance with the teachings of the above described U.S. Pat. Nos. 4,969,888 and 5,108,404. For a given vertebral body 26, access into the interior volume 30 can be accomplished, for example, by drilling an access portal 43 through either or both pedicles 42. FIG. 4 shows a single transpedicular approach in lateral view, and FIG. 5 shows a single transpedicular approach in coronal view. As FIG. 4 shows, the access portal 43 for a transpedicular approach enters at the top of the vertebral body 26, where the pedicle 42 is relatively thin, and extends at an angle downward toward the bottom of the vertebral structure 26 to enter the interior volume 30. The catheter tube 12 carrying the expandable structure 20 is guided into the interior volume 30 through an outer guide sheath 24, which passes through the portal 43.

Figure 6:
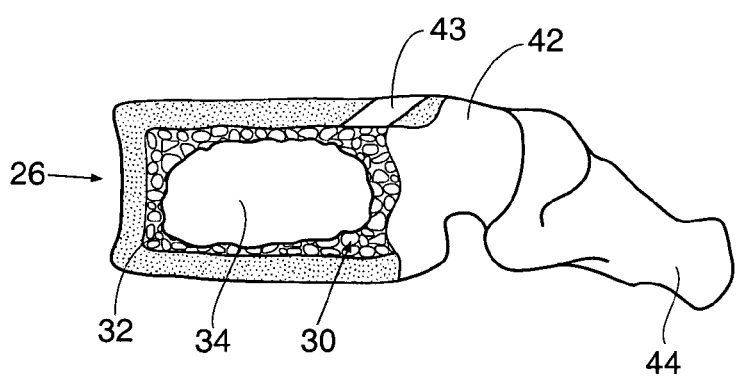
FIG. 6 is a lateral view of the lumbar vertebra shown in FIG. 4, after expansion of the expandable structure shown in FIG. 1 to form a cavity.

As FIG. 6, expansion of the structure 20 in the interior volume 30 compresses the cancellous bone 32 and creates an interior cavity 34. The cavity 34 remains after collapse and removal of the structure 20 from the interior volume 30. The cavity 34 is intended to receive a filling material, like bone cement, to provide renewed interior structural support for surrounding cortical bone 28. The compaction of cancellous bone also exerts interior force upon cortical bone 28, making it possible to elevate or push broken and compressed bone back to or near its original prefracture, or other desired, condition.

Access to the interior volume 30 of a given vertebral body 26 can be achieved through the sides of the body, shown in phantom lines 45 in FIG. 5. This approach is called a posterolateral approach.

The above described access can be carried out in a minimally invasive manner. It can also be carried out using an open surgical procedure. Using open surgery, the physician can approach the bone to be treated as if the procedure is percutaneous, except that there is no skin and other tissues between the surgeon and the bone being treated. This keeps the cortical bone as intact as possible, and can provide more freedom in accessing the interior volume 30 of the vertebral body.

Figure 7:
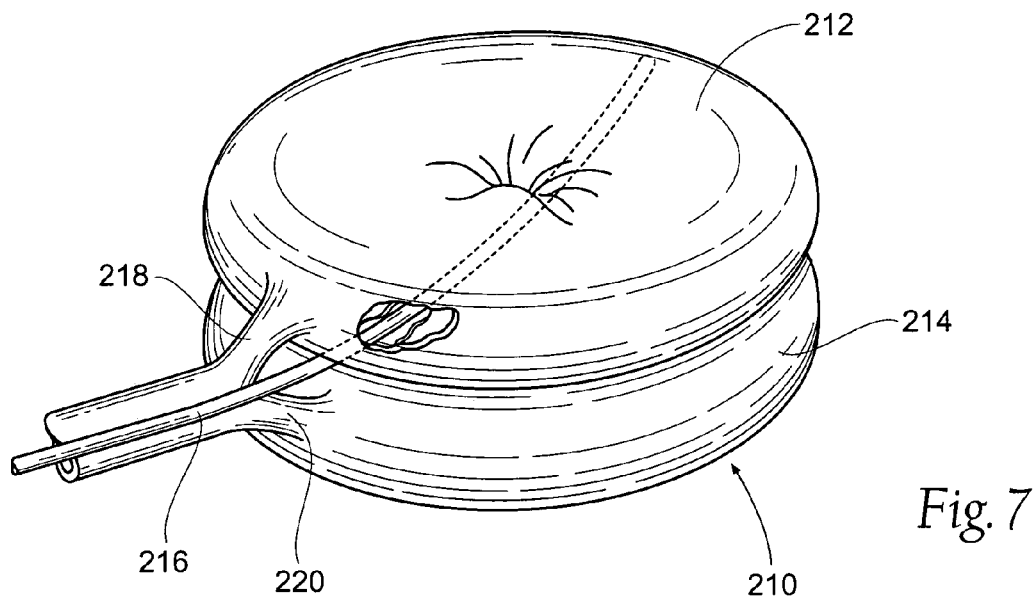
FIG. 7 is a perspective view of one representative embodiment of an expandable structure having a stacked doughnut-shaped geometry.

A. Representative Embodiments of Expandable Structures to Treat Vertebrae i. Constrained Donut-Shaped Geometries FIG. 7 shows a representative embodiment of an expandable structure, which is broadly denoted by the numeral 210. The structure 210 comprises a pair of hollow, inflatable, non-expandable parts 212 and 214 of flexible material, such as PET or Kevlar. Parts 212 and 214 have a suction tube 216 therebetween for drawing fats and other debris by suction into tube 216 for transfer to a remote disposal location. The suction tube 216 has one or more suction holes so that suction may be applied to the open end of tube 216 from a suction source (not shown).

The parts 212 and 214 are connected together by an adhesive which can be of any suitable type. Parts 212 and 214 are doughnut-shaped, as shown in FIG. 7, and have tubes 218 and 220 which communicate with and extend away from the parts 212 and 214, respectively, to a source of inflating liquid under pressure (not shown). The liquid expands the structure 210.

Figure 8:
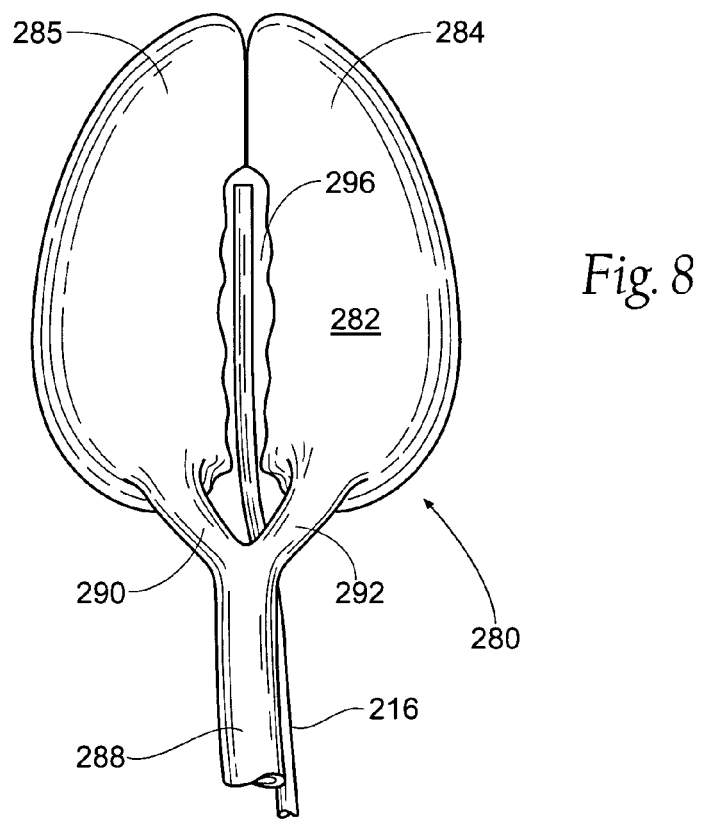
FIG. 8 is a view of another representative embodiment of an expandable structure having an oblong-shaped geometry.

FIG. 8 shows a modified doughnut shape structure 280 of the type shown in FIG. 7, except the doughnut shapes of structure 280 are not stitched onto one another. In FIG. 8, structure 280 has a pear-shaped outer convex surface 282 which is made up of a first hollow part 284 and a second hollow part 285. A tube 288 is provided for directing liquid into the two parts along branches 290 and 292 to inflate the parts after the parts have been inserted into the interior volume of a bone. A catheter tube 216 may or may not be inserted into the space 296 between two parts of the balloon 280 to provide irrigation or suction. An adhesive bonds the two parts 284 and 285 together.

Figure 9:
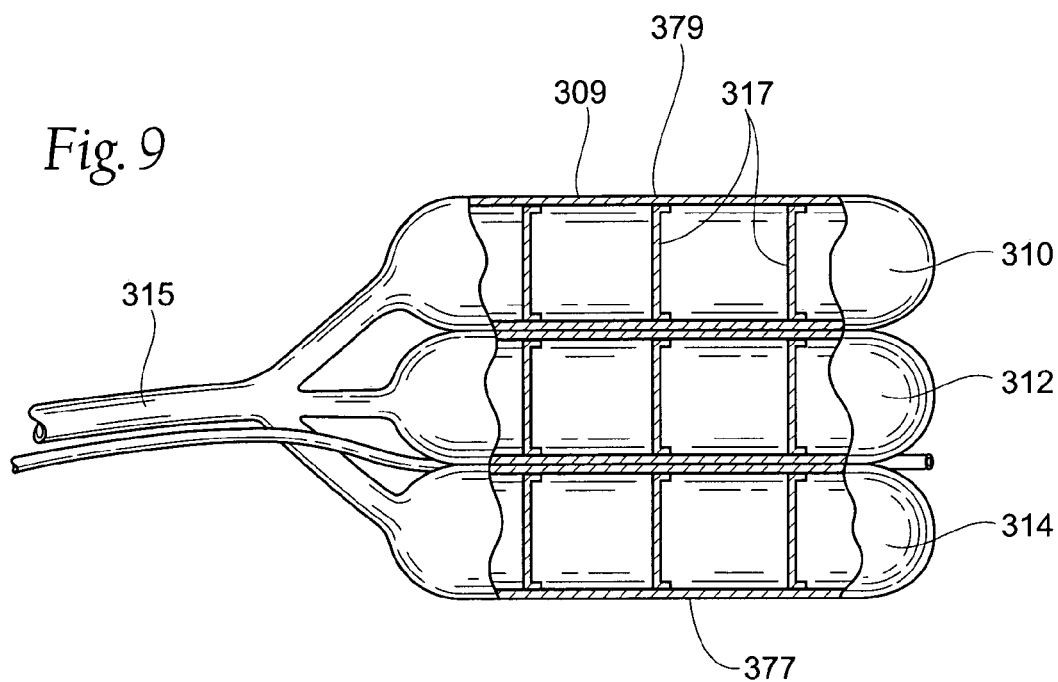
FIG. 9 is an elevation view of another representative embodiment of an expandable structure showing three stacked structures and string-like restraints for limiting the expansion of the bodies during inflation.

FIG. 9 shows another representative embodiment of an expandable structure, designated 309. The structure 309 has a generally round geometry and three expandable structure units 310, 312 and 314. The structure units 310, 312, and 314 include string-like external restraints 317, which limit the expansion of the structure units 310, 312, and 314 in a direction transverse to the longitudinal axes of the structure units 310, 312, and 314. The restraints 317 are made of the same or similar material as that of the structure units 310, 312, and 314, so that they have some resilience but substantially no expansion capability.

A tubes 315 direct liquid under pressure into the structure units 310, 312 and 314 to expand the units and cause compaction of cancellous bone. The restraints 317 limit expansion of the structure units prior to failure, keeping the opposed sides 377 and 379 substantially flat and parallel with each other.

ii. Constrained Kidney-Shaped Geometries

Figure 10:
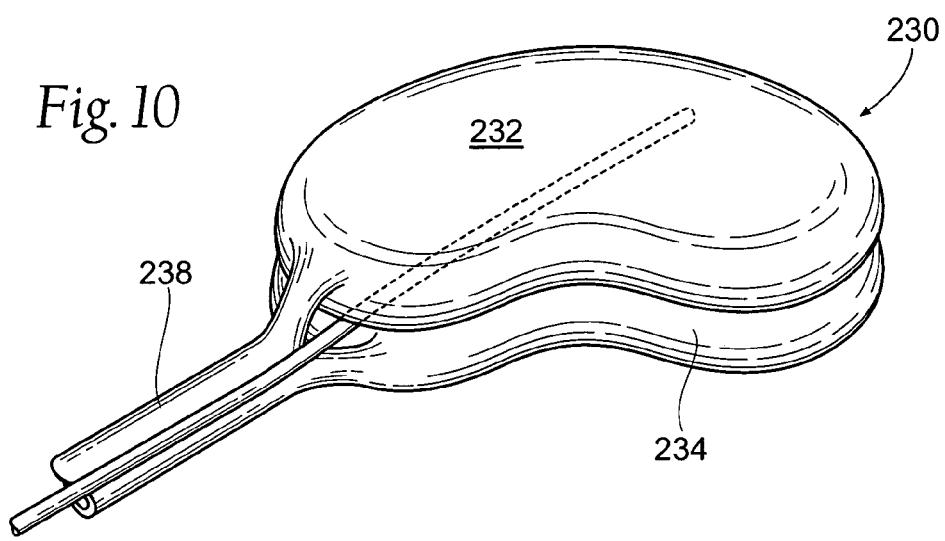
FIG. 10 is a perspective view of another representative embodiment of an expandable structure having a kidney bean-shaped geometry.

FIG. 10 shows another representative embodiment of an expandable structure 230, which has a kidney-shaped geometry. The structure 230 has a pair of opposed kidney-shaped side walls 232 and a continuous end wall 234. A tube 238 directs liquid into the structure to expand it within the vertebral structure.

Figure 11:
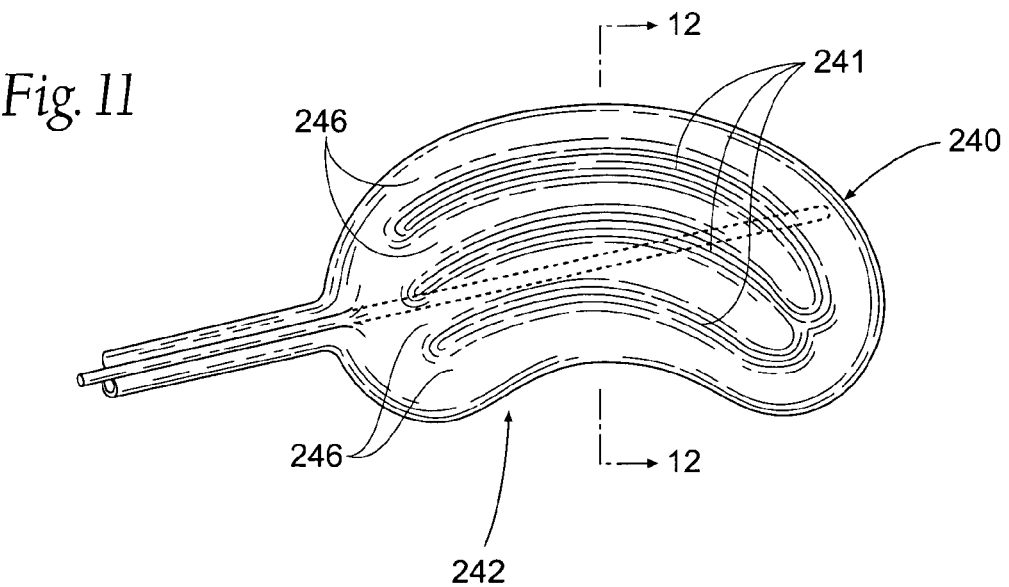
FIG. 11 is a top view of another representative embodiment of an expandable structure having a kidney bean-shaped geometry with several compartments formed by a heating element or branding tool.
Figure 12:
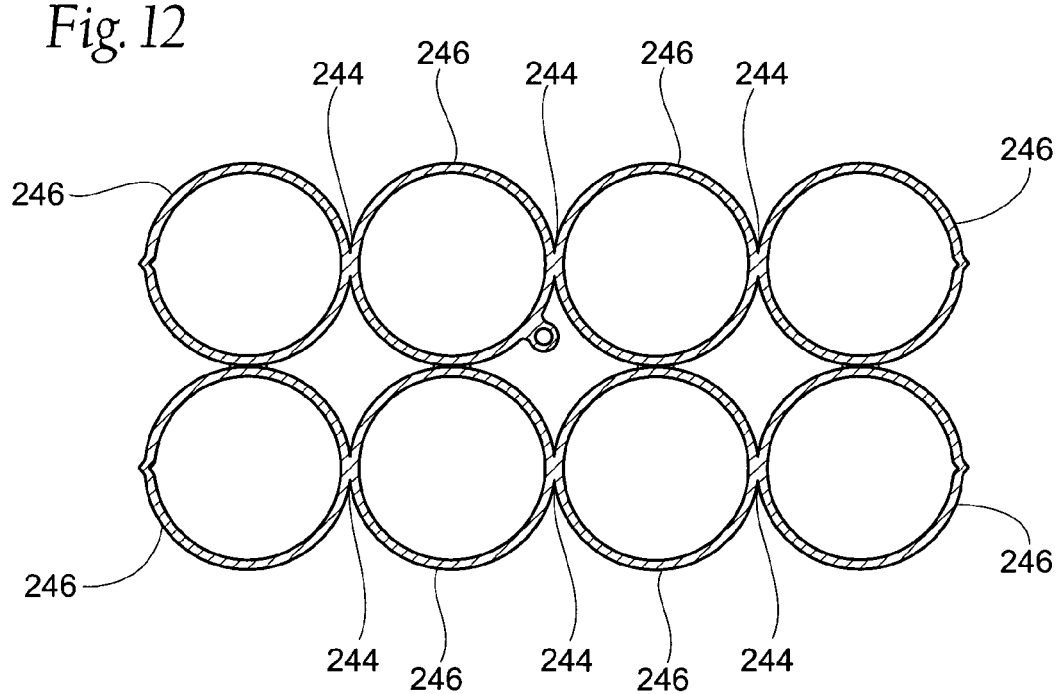
FIG. 12 is a cross-sectional view taken along line 12—12 of FIG. 11.

FIG. 11 shows another representative embodiment of an expandable structure 242, which also has a kidney-shaped geometry. The structure 242 is initially a single chamber bladder, but the bladder is branded along curved lines or strips 241 to form attachment lines 244 which take the shape of side-by-side compartments 246, as shown in FIG. 12. A similar pattern of strips as in 242, but in straight lines would be applied to a structure that is square or rectangular. The branding causes a welding of the two sides of the bladder to occur.

The details of these and other expandable structures usable to treat vertebral bodies are described in U.S. patent application Ser. No. 08/188,224, filed Jan. 26, 1994, and U.S. patent application Ser. No. 08/871,114, filed Jun. 9, 1997, which are incorporated herein by reference.

B. Selection of Desired Geometry

The eventual selection of the size and shape of a particular expandable structure 20 or structures to treat a targeted vertebral structure 26 is based upon several factors. When multiple expandable bodies are used, the total combined dimensions of all expandable bodies deployed, when substantially expanded, should be taken into account.

The anterior-posterior (A-P) dimension (see FIG. 13) for the expandable structure or bodies is selected from the CT scan or plain film or x-ray views of the targeted vertebral structure 26. The A-P dimension is measured from the internal cortical wall of the anterior cortex to the internal cortical wall of the posterior cortex of the vertebral structure. In general, the appropriate A-P dimension for the expandable structure or bodies is less than this anatomic measurement.

The appropriate side to side dimension L (see FIG. 13) for an expandable structure or bodies is also selected from the CT scan, or from a plain film or x-ray view of the targeted vertebral structure. The side to side distance is measured between the internal cortical walls laterally across the targeted vertebral structure. In general, the appropriate side to side dimension L for the expandable structure is less than this anatomic measurement.

The lumbar vertebral structure tends to be much wider in side to side dimension L then in A-P dimension. In thoracic vertebral bodies, the side to side dimension and the A-P dimensions are almost equal.

The height dimensions H of the expandable structure or bodies (see FIG. 13) is chosen by the CT scan or x-ray views of the vertebral bodies above and below the vertebral structure to be treated. The height of the vertebral bodies above and below the vertebral structure to be treated are measured and averaged. This average is used to determine the appropriate height dimension of the chosen expandable structure.

The dimensions of expandable structure or bodies for use in vertebrae are patient specific and will vary across a broad range, as summarized in the following table:

| Vertebra Type | Height (H) Dimension of Typical Expandable structure or Bodies | Posterior (A-P) Dimension of Typical Expandable Structure or Bodies | Side to Side Dimension (L) of Typical Expandable Structure or Bodies |
| --- | --- | --- | --- |
| Lumbar | 0.5 cm to 4.0 cm | 0.5 cm to 4.0 cm | 0.5 cm to 5.0 cm |
| Thoracic | 0.5 cm to 3.5 cm | 0.5 cm to 3.5 cm | 0.5 cm to 4.0 cm |

A preferred expandable structure for use in a vertebral structure is stacked with two or more expandable members of unequal height (designated 20A and 20B in FIG. 13), where each member can be separately inflated through independent tube systems. The total height of the stack when fully inflated should be within the height ranges specified above. Such a design allows the fractured vertebral structure to be returned to its original height in steps, which can be easier on the surrounding tissue, and it also allows the same balloon to be used in a wider range of vertebral structure sizes.

III. Treatment of Other Bones

Like vertebrae, the interior regions of other bones in the appendicular skeleton are substantially occupied by cancellous bone, and thus can be treated with the use of one or more expandable structures. Regions in the appendicular skeleton which can be treated using expandable structures include the distal radius, the proximal tibial plateau, the proximal humerus, the proximal femoral head, and the calcaneus.

As for vertebral bodies, expandable structures possess the important attribute of being able, in the course of forming cavities by compressing cancellous bone, to also elevate or push broken or compressed cortical bone back to or near its normal anatomic position. This is a particularly important attribute for the successful treatment of compression fractures or cancellous bone fractures in the appendicular skeleton, such as the distal radius, the proximal humerus, the tibial plateau, the femoral head, hip, and calcaneus.

One representative example of an expandable structure for the treatment of cancellous bone regions of a long bone (distal radius) will be described.

A. Expandable Structure for the Distal Radius

The selection of an appropriate expandable to treat a fracture of the distal radius will depend on the radiological size of the distal radius and the location of the fracture.

FIGS. 14 and 15 show a representative expandable structure 260 for use in the distal radius. The structure 260, which is shown deployed in the distal radius 252, has a shape which approximates a pyramid but more closely can be considered the shape of a humpbacked banana. The geometry of the structure 260 substantially fills the interior of the space of the distal radius to compact cancellous bone 254 against the inner surface 256 of cortical bone 258.

The structure 260 has a lower, conical portion 259 which extends downwardly into the hollow space of the distal radius 252. This conical portion 259 increases in cross section as a central distal portion 261 is approached. The cross section of the structure 260 is shown at a central location (FIG. 14), which is near the widest location of the structure 260. The upper end of the structure 260, denoted by the numeral 262, converges to the catheter tube 288 for directing a liquid into the structure 260 to expand it and force the cancellous bone against the inner surface of the cortical bone.

The shape of the structure 260 is determined and restrained by tufts formed by string restraints 265. These restraints are optional and provide additional strength to the structure 260, but are not required to achieve the desired configuration.

The structure 260 is placed into and taken out of the distal radius in the same manner as that described above with respect to the vertebral bone.

Typical dimensions of the distal radius structure vary as follows:

The proximal end of the structure 260 (i.e. the part nearest the elbow) is cylindrical in shape and will vary from 0.4×0.4 cm to 1.8×1.8 cm.

The length of the distal radius structure will vary from 1.0 cm to 12.0 cm.

The widest medial to lateral dimension of the distal radius structure, which occurs at or near the distal radio-ulnar joint, will measure from 0.5 cm to 2.5 cm.

The distal anterior-posterior dimension of the distal radius structure will vary from 0.4 to 3.0 cm.

The details of these and other expandable structures usable to treat vertebral bodies are described in U.S. patent application Ser. No. 08/188,224, filed Jan. 26, 1994, and U.S. patent application Ser. No. 08/871,114, filed Jun. 9, 1997, which are incorporated herein by reference.

IV. DEFLECTION OF AN EXPANDABLE STRUCTURE

Figure 16:
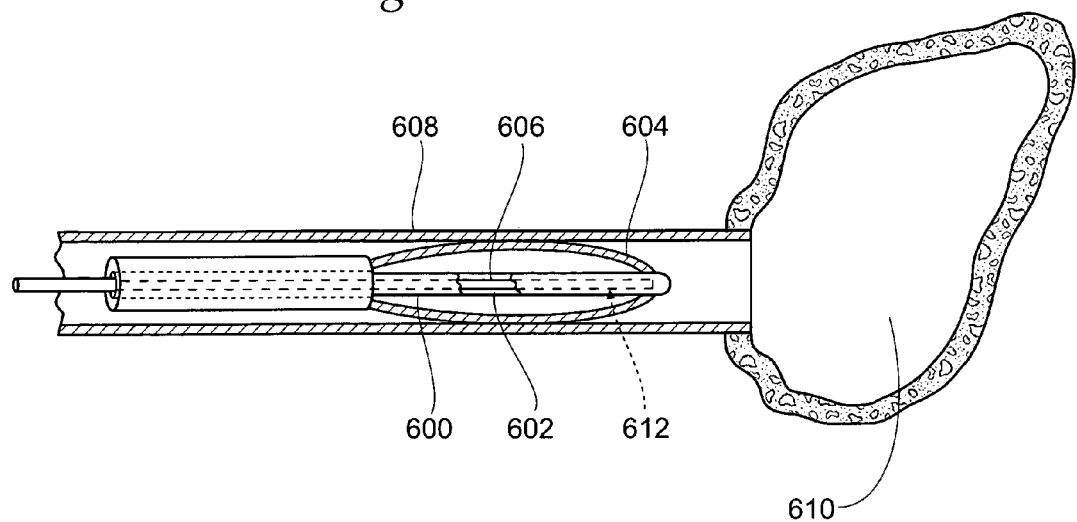
FIG. 16 is a side view, with parts broken away and in section, of an expandable structure having an enclosed stiffening member, to straighten the structure during passage through a guide sheath into an interior body region.

As FIG. 16 shows, a selected expandable structure 604 can include an enclosed tube 600, which provides an interior lumen 602 passing within the expandable structure 604. The lumen 602 accommodates the passage of a stiffening member or stylet 606 made, e.g., from stainless steel or molded plastic material.

The presence of the stylet 606 serves to keep the structure 604 in the desired distally straightened condition during passage through an associated guide sheath 608 toward the targeted body region 610, as FIG. 16 shows. As before explained, access to the targeted body region 610 through the guide sheath 608 can be accomplished using a closed, minimally invasive procedure or with an open procedure.

Figure 17:
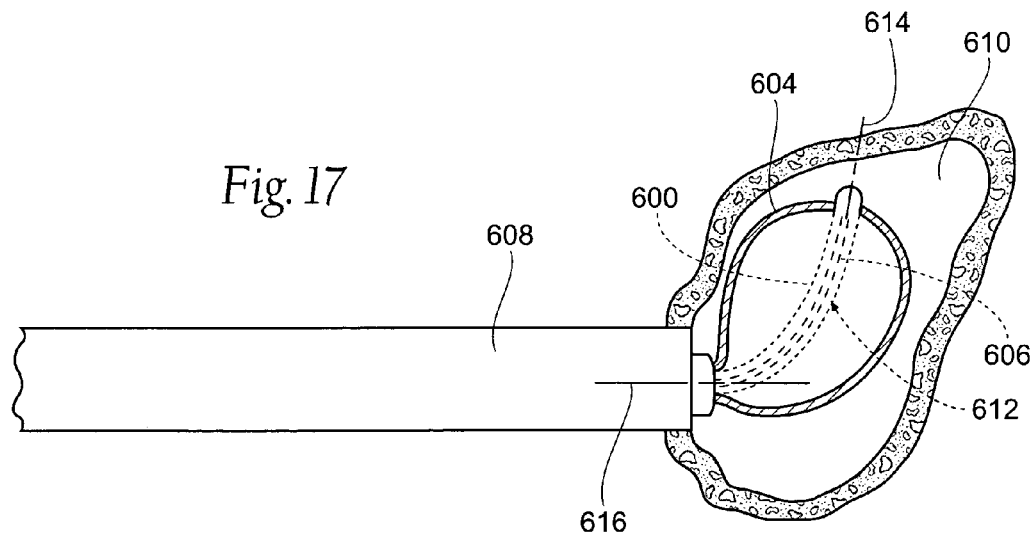
FIG. 17 is a side view of the expandable structure shown in FIG. 16, after deployment beyond the guide sheath and into the interior body region, in which the stiffening member includes a distal region having a preformed bend, which deflects the structure relative to the axis of the guide sheath.

As shown in FIG. 17, the stylet 606 can have a preformed memory, to normally bend the distal region 612 of the stylet 606. The memory is overcome to straighten the stylet 606 when confined within the guide sheath 608, as FIG. 16 shows. However, as the structure 604 and stylet 606 advance free of the guide sheath 608 and pass into the targeted region 610, the preformed memory bends the distal stylet region 612. The bend of the distal stylet region 612 bends the tube 600 and thereby shifts the axis 614 of the attached expandable structure 604 relative to the axis 616 of the access path (i.e., the guide sheath 608). The prebent stylet 606, positioned within the interior of the structure 604, aids in altering the geometry of the structure 604 in accordance with the orientation desired when the structure 604 is deployed for use in the targeted region 610.

V. SINGLE USE

Expansion of any one of the expandable structures described herein during first use in a targeted structure region generates stress on the material or materials which make up the structure. The material stress created by operational loads during first use in a targeted structure region can significantly alter the molded morphology of the structure, making future performance of the structure unpredictable.

For example, expansion within bone during a single use creates contact with surrounding cortical and cancellous bone. This contact can damage the structure, creating localized regions of weakness, which may escape detection. The existence of localized regions of weakness can unpredictably cause overall structural failure during a subsequent use.

In addition, exposure to blood and tissue during a single use can entrap biological components on or within the structure or the associated catheter tube. Despite cleaning and subsequent sterilization, the presence of entrapped biological components can lead to unacceptable pyrogenic reactions.

As a result, following first use, the structure can not be relied upon to reach its desired configuration during subsequent use and may not otherwise meet established performance and sterilization specifications. The effects of material stress and damage caused during a single use, coupled with the possibility of pyrogen reactions even after resterilization, reasonably justify imposing a single use restriction upon devices which carry these expandable structures for deployment in bone.

Figure 18:
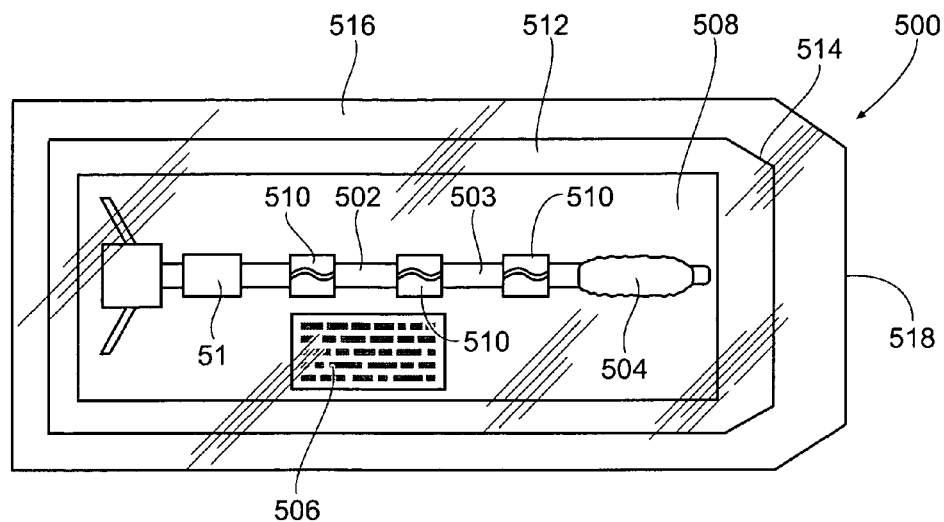
FIG. 18 is a plan view of a sterile kit to store a single use probe, which carries an expandable structure of the type previously shown.
Figure 19:
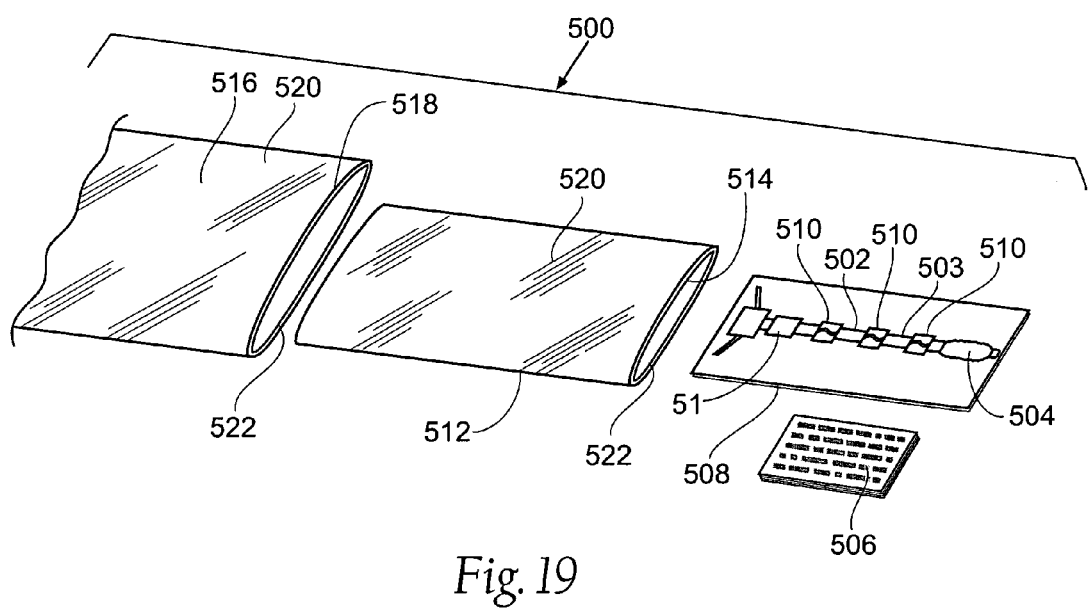
FIG. 19 is an exploded perspective view of the sterile kit shown in FIG. 18.

To protect patients from the potential adverse consequences occasioned by multiple use, which include disease transmission, or material stress and instability, or decreased or unpredictable performance, the invention also provides a kit 500 (see FIGS. 18 and 19) for storing a single use probe 502, which carries an expandable structure 504 described herein prior to deployment in bone.

In the illustrated embodiment (see FIGS. 18 and 19), the kit 500 includes an interior tray 508. The tray 508 holds the probe 502 in a lay-flat, straightened condition during sterilization and storage prior to its first use. The tray 508 can be formed from die cut cardboard or thermoformed plastic material. The tray 508 includes one or more spaced apart tabs 510, which hold the catheter tube 503 and expandable structure 504 in the desired lay-flat, straightened condition. As shown, the facing ends of the tabs 510 present a nesting, serpentine geometry, which engages the catheter tube 503 essentially across its entire width, to securely retain the catheter tube 503 on the tray 508.

The kit 500 includes an inner wrap 512, which is peripherally sealed by heat or the like, to enclose the tray 508 from contact with the outside environment. One end of the inner wrap 512 includes a conventional peal-away seal 514 (see FIG. 19), to provide quick access to the tray 508 upon instance of use, which preferably occurs in a sterile environment, such as within an operating room.

The kit 500 also includes an outer wrap 516, which is also peripherally sealed by heat or the like, to enclosed the inner wrap 512. One end of the outer wrap 516 includes a conventional peal-away seal 518 (see FIG. 19), to provide access to the inner wrap 512, which can be removed from the outer wrap 516 in anticipation of imminent use of the probe 502, without compromising sterility of the probe 502 itself.

Both inner and outer wraps 512 and 516 (see FIG. 19) each includes a peripherally sealed top sheet 520 and bottom sheet 522. In the illustrated embodiment, the top sheet 520 is made of transparent plastic film, like polyethylene or MYLAR™ material, to allow visual identification of the contents of the kit 500. The bottom sheet 522 is made from a material that is permeable to EtO sterilization gas, e.g., TYVEC™ plastic material (available from DuPont).

The sterile kit 500 also carries a label or insert 506, which includes the statement "For Single Patient Use Only" (or comparable language) to affirmatively caution against reuse of the contents of the kit 500. The label 506 also preferably affirmatively instructs against resterilization of the probe 502. The label 506 also preferably instructs the physician or user to dispose of the probe 502 and the entire contents of the kit 500 upon use in accordance with applicable biological waste procedures.

The presence of the probe 502 packaged in the kit 500 verifies to the physician or user that probe 502 is sterile and has not be subjected to prior use. The physician or user is thereby assured that the expandable structure 504 meets established performance and sterility specifications, and will have the desired configuration when expanded for use.

The features of the invention are set forth in the following claims.

We claim:

1. A method comprising
    selecting a vertebral body for treatment having a cortical wall enclosing a cancellous bone volume,
    providing a void creation device including an expandable structure adapted to undergo expansion in the cancellous bone volume, the expandable structure having at least one dimension so that the expandable structure will assume a predetermined shape and size when substantially expanded that compacts only a first volume of the cancellous bone volume to form a void, leaving a second volume of the cancellous bone volume substantially uncompacted by the expandable structure,
    introducing the void creation device into the vertebral body through a percutaneous access path,
    expanding the expandable structure in the cancellous bone volume to the predetermined shape and size to create the void,
    leaving the second volume of the cancellous bone volume substantially uncompacted by the expandable structure, and
    placing a filling material within the void through the percutaneous access path.

2. A method according to claim 1,
    wherein the first volume of the cancellous bone volume comprises about 30% to 90% of the cancellous bone volume.

3. A method according to claim 1 wherein the first volume of the cancellous bone volume comprises about 40% to 90% of the cancellous bone volume.

4. A method according to claim 1 wherein the structure comprises an inflatable body.

5. A method according to claim 1 wherein the structure comprises a balloon.

6. A method according to claim 1 wherein the filling material placed within the void hardens within the void.

7. A method according to claim 1, further including removing the structure from the void.

* * * * *

UNITED STATES PATENT AND TRADEMARK OFFICE
CERTIFICATE OF CORRECTION

PATENT NO. : 7,044,954 B2
APPLICATION NO. : 09/884365
DATED : May 16, 2006
INVENTOR(S) : Mark A. Reiley et al.

It is certified that error appears in the above-identified patent and that said Letters Patent is hereby corrected as shown below:

On the face of the issued patent under U.S. Patent Documents insert:
4,878,495    7 Nov 1989    Grayzel
4,909,252    20 Mar 1990   Goldberger
5,049,132    17 Sep 1991   Shaffer et al.

On the face of the issued patent under Other Prior Art insert:
Aebi, M., "The Internal Skeletal Fixation System. A New Treatment of Thoracolumbar Fractures and Other Spinal Disorders," Clin. Orthop., Vol. 227, pp. 30-43 (1988)
Blauth, M., "Therapeutic Concept and Results of Operative Treatment in Acute Trauma of the Thoracic and Lumbar Spine: The Hannover Experience, " J. of Orthop. Trauma, Vol. 1, No. 3 pp. 240-52 (1987)

Signed and Sealed this

Twenty-second Day of August, 2006

JON W. DUDAS
*Director of the United States Patent and Trademark Office*